United States Patent
Ricol et al.

(10) Patent No.: US 8,328,773 B2
(45) Date of Patent: Dec. 11, 2012

(54) IMPLANTABLE SITE WITH SEPTUM PRESTRESSED IN TWO DIRECTIONS

(75) Inventors: Jean-Paul Ricol, Lyon (FR); Pascal Paganon, Lyon (FR)

(73) Assignee: Compagnie Europeenne d'Etude et de Recherche de Dispositifs pour l'Impantation par Laparoscopie, Vienne (FR)

( * ) Notice: Subject to any disclaimer, the term of this patent is extended or adjusted under 35 U.S.C. 154(b) by 0 days.

(21) Appl. No.: 13/119,565

(22) PCT Filed: Sep. 17, 2009

(86) PCT No.: PCT/EP2009/062051
§ 371 (c)(1), (2), (4) Date: Mar. 17, 2011

(87) PCT Pub. No.: WO2010/031812
PCT Pub. Date: Mar. 25, 2010

(65) Prior Publication Data
US 2011/0172595 A1    Jul. 14, 2011

(30) Foreign Application Priority Data
Sep. 18, 2008   (FR) ...................................... 08 05146

(51) Int. Cl.
*A61M 31/00*    (2006.01)

(52) U.S. Cl. .............................. 604/288.02; 604/288.01
(58) Field of Classification Search ............. 604/288.01, 604/288.02, 288.04, 93.01
See application file for complete search history.

(56) References Cited

U.S. PATENT DOCUMENTS

| 5,328,465 A * | 7/1994 | Kratoska et al. ......... 604/288.02 |
| 2008/0119798 A1* | 5/2008 | Chantriaux et al. ..... 604/288.02 |

FOREIGN PATENT DOCUMENTS

| FR | 2 905 603 | 3/2008 |
| WO | WO 2006/021695 | 3/2006 |
| WO | WO 2008/029010 | 3/2008 |

* cited by examiner

*Primary Examiner* — Laura Bouchelle
(74) *Attorney, Agent, or Firm* — Occhiuti Rohlicek & Tsao LLP

(57) ABSTRACT

The invention relates to an implantable medical device (1) for injecting and/or collecting fluid substance into and/or from an organism and comprising a chamber (2) delimited by a wall (3) which has at least one pierceable portion (4) in the area of which said wall (3) can be pierced through in the direction of its thickness (e) by a needle (5), said device comprising means (10) for transverse compression of the pierceable portion (4), and also retention means (20) designed to oppose the buckling, towards the outside of the device, experienced by the pierceable portion (4) under the effect of the compression (F1).

16 Claims, 3 Drawing Sheets

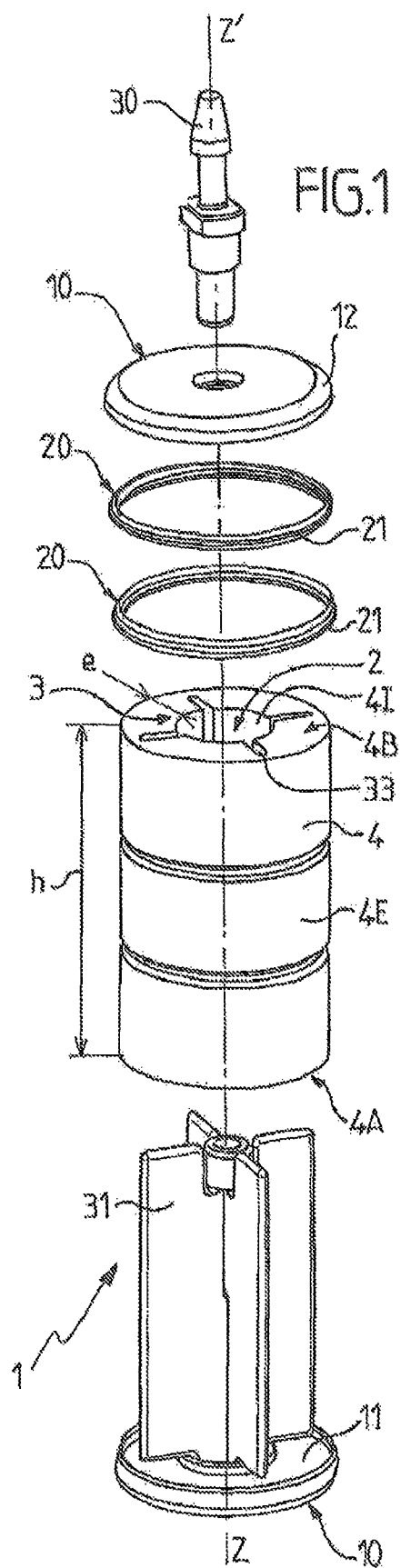
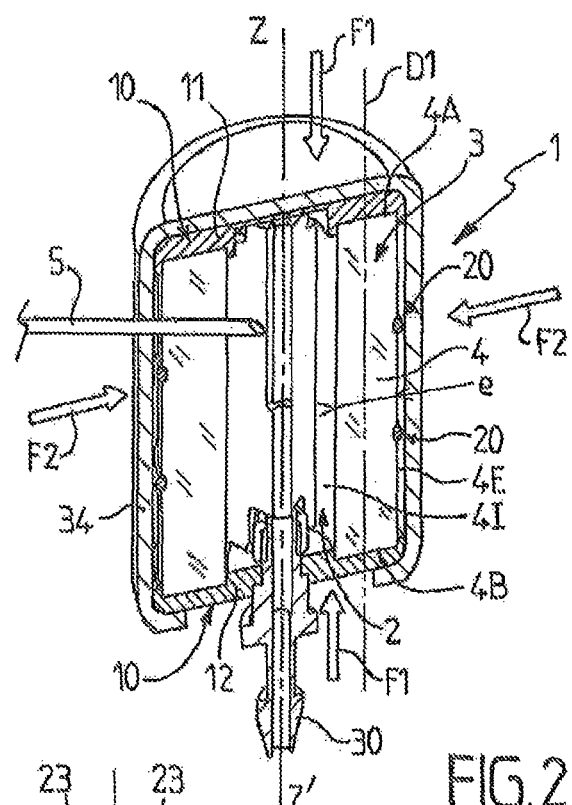
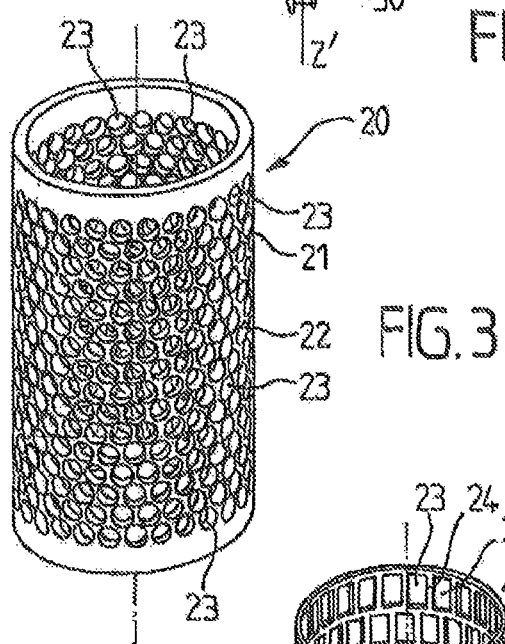
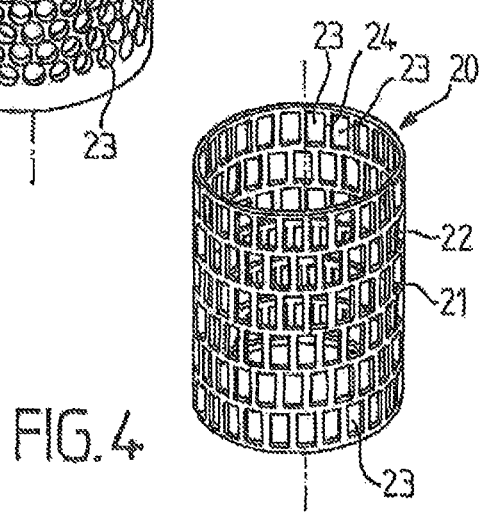

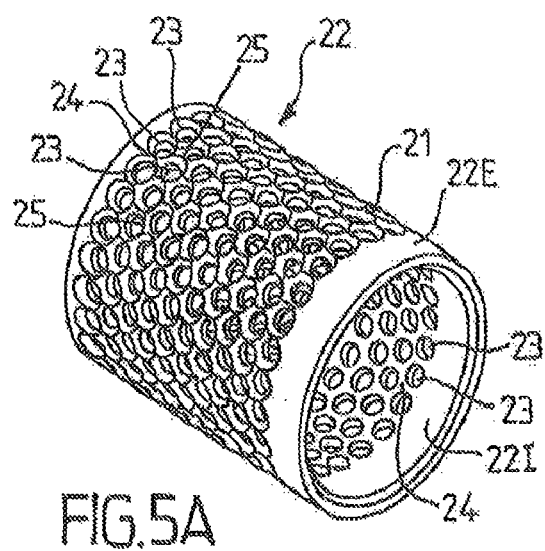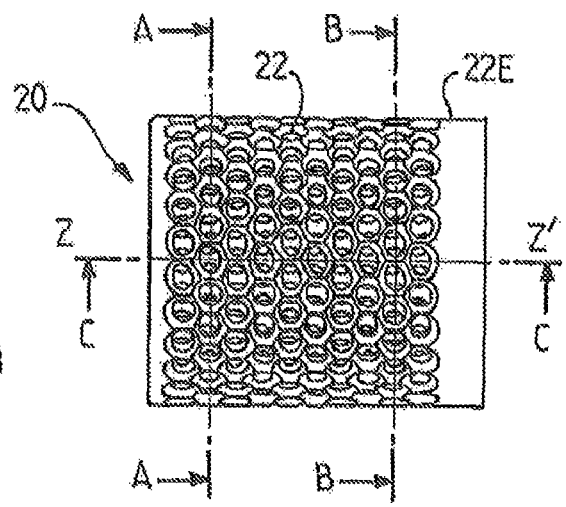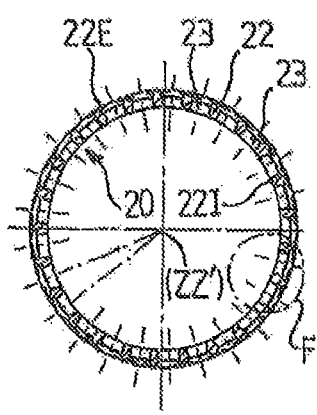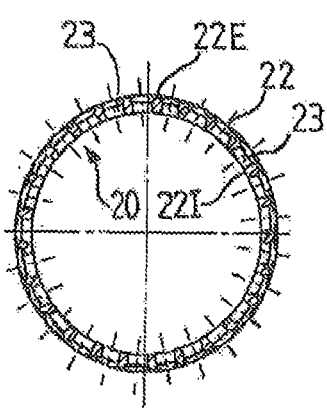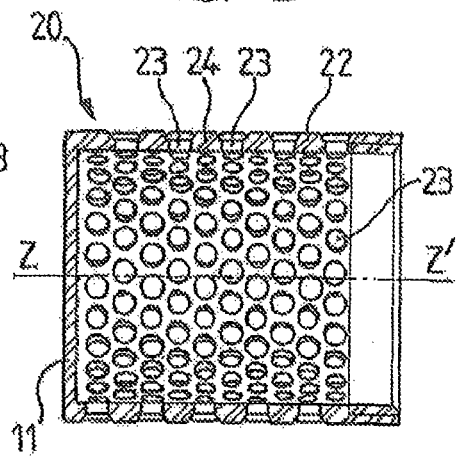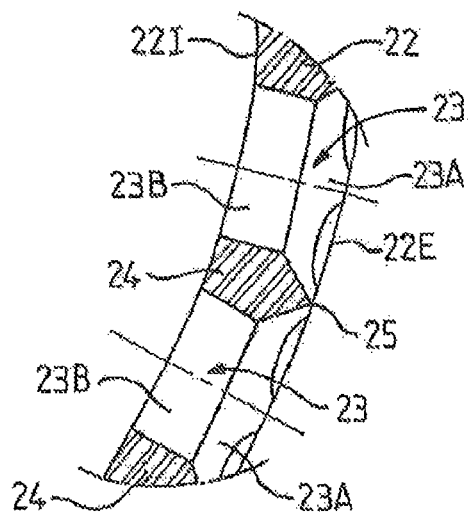

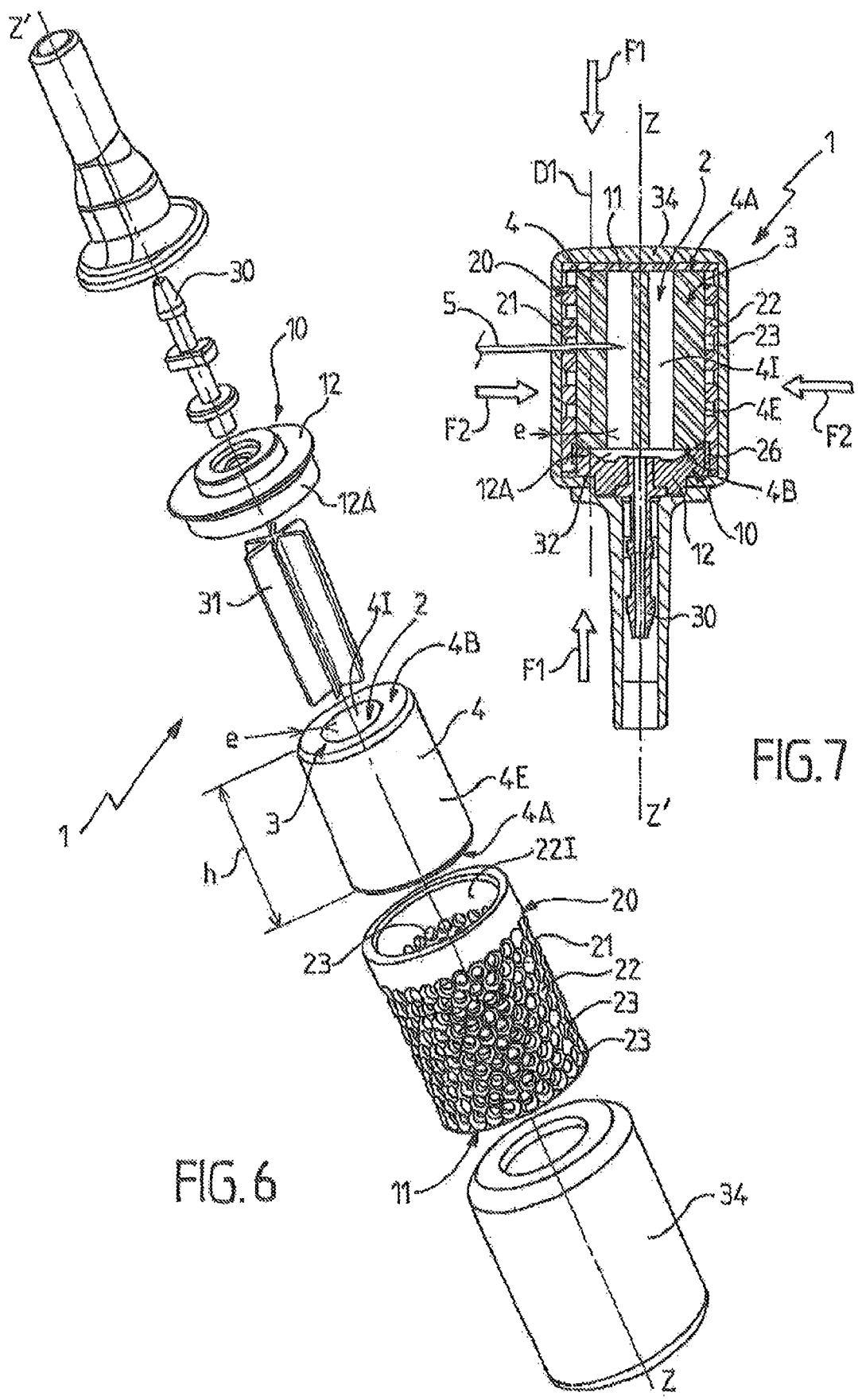

IMPLANTABLE SITE WITH SEPTUM PRESTRESSED IN TWO DIRECTIONS

CROSS REFERENCE TO RELATED APPLICATIONS

This application is the national stage entry under 35 USC 371 for: PCT/EP2009/062051, filed on Sep. 17, 2009, which claims the benefit of the Sep. 18, 2008 priority date of French application FR0805146. The contents of both the foregoing applications are incorporated herein by reference.

The invention relates to implantable medical devices for injecting and/or collecting fluid substances into and/or from a patient's body, these devices being known as "implantable sites".

The present invention pertains more particularly to an implantable medical device designed for the injection and/or collection of fluid substance into and/or from a human or animal organ, the device comprising a chamber designed to receive said fluid substance, said chamber being demarcated by a wall having at least one penetrable portion at which said wall can be pierced through its thickness by a needle designed to inject fluid substance into the chamber or collect fluid substance from the chamber, said device comprising means for transversally compressing the penetrable portion, the means being arranged so as to compressively stress said penetrable portion along at least one first direction that is substantially transversal to the direction of the thickness of the wall.

There are known ways of implanting a medical device called an "implantable site" beneath a patient's skin, this device being designed to form a remote point of access enabling the transfer of substances to or from the blood circulation system, the tissues of an organ or again, an inflatable implant such as a balloon or a constriction ring.

Generally, an implantable site of this kind takes the form of a casing in which a chamber is made, this chamber communicating with a flexible catheter connecting said casing to the target area for which the injected substance is intended, or from which the collected substance comes.

In order to allow access to the chamber by a hollow needle, the wall of the casing generally has a removal area formed by a self-sealing membrane or "septum" made out of an elastomer so that the imperviousness or tight sealing quality of the site is preserved both when the needle pierces the wall and when the needle is withdrawn from the wall, the hole formed by said needle automatically closing, when the needle is extracted, by a phenomenon of elastic self-healing.

Although they give appreciable results in facilitating the operations of injection and collection, the prior-art implantable sites sometimes have non-negligible drawbacks.

Indeed, in order to ensure their mechanical worthiness as well as their imperviousness when pierced several times, prior-art sites are generally provided with relatively thick, self-sealing membranes of small expanse so that they can be inserted by force into a housing made in the casing that pre-stresses them compressively in a direction substantially transversal to the normal direction of penetration of the needle.

Prior-art removal areas therefore often have a relatively small useful area and accessibility when compared with the overall space taken up by the implantable site.

In addition, the manufacturing tolerances as regards dimensions and quality for prior-art septums are generally broad so that, prior to the operations for assembling the implantable site, it is first of all necessary to make a rigorous selection of the septum on the basis of its dimensions as well as its hardness, so as to ensure that it can be appropriately assembled with the casing while at the same time ensuring the requisite degree of imperviousness.

Naturally, these selection and control steps tend to lengthen and complicate the production cycle, to the detriment of the cost price of the device.

The objects assigned to the present invention are therefore aimed at mitigating the above-mentioned drawbacks and at proposing a novel implantable medical device for injecting and/or collecting fluid substance into or from a human or animal organism, the device having optimized and particularly lasting imperviousness.

Another object assigned to the invention is aimed at proposing a novel implantable medical device that is very easily accessible to the practitioner after implantation.

Another object assigned to the invention is aimed at proposing a novel atraumatic implantable medical device that minimizes the discomfort caused to the patient.

Another object assigned to the invention is aimed at proposing a novel implantable medical device with a particularly simple and compact structure.

Another object assigned to the invention proposes a novel implantable medical device which costs little to manufacture, is simple to assemble and is particularly tolerant to heterogeneities in the manufacture of its different components.

The objects assigned to the invention are achieved by means of an implantable medical device for injecting and/or collecting fluid substance into or from a human or animal organism, the device comprising a chamber for receiving said fluid substance, said chamber being demarcated by a wall which has at least one penetrable portion at which said wall can be pierced through in the direction of its thickness by a needle designed to inject and/or remove the fluid substance into or from the chamber, said device comprising means for transversally compressing the penetrable portion, these means being arranged so as to stress said penetrable portion compressively along a first direction that is substantially transversal to the direction of thickness of the wall, said device being characterized in that it is provided with retaining means designed to counter the buckling of the penetrable portion towards the exterior of the device under the effect of the compression exerted by the transversal compression means.

Other objects and characteristics of the invention shall appear in greater detail from the following description as well as from the appended drawings, provided by way of a purely illustrative and non-exhaustive example, of which:

FIG. 1 is an exploded view in perspective of a first embodiment of the implantable medical device according to the invention, FIG. 2 is a cutaway view in perspective in a longitudinal plane of the medical device of FIG. 1 in an assembled configuration, FIG. 3 and FIG. 4 illustrate views in perspective of two alternative embodiments of the retaining means according to the invention, FIGS. 5A, 5B, 5C, 5D, 5E and 5F represent another embodiment of retaining means compliant with the invention, seen respectively in perspective, a side view, a first cross-section and a second cross-section, a longitudinal section and a detailed magnified cross-section, FIG. 6 is an exploded view in perspective of a second embodiment of an implantable medical device according to the invention within which the retaining means illustrated in the FIGS. 5A to 5F are implemented.

FIG. 7 is an illustration in a longitudinal section of the medical device corresponding to the second embodiment of an implantable medical device shown in FIG. 6.

The invention pertains to an implantable medical device 1 for injecting and/or removing fluid substances into or from a human organism or animal organism.

A device 1, also called an "implantable site", is designed to be implanted surgically in a patient's body, preferably beneath said patient's skin in order to constitute a point of access for introducing or extracting fluid substances into or from the patient's body.

The device 1 can be implemented and adapted to various uses.

In particular, the device 1 of the invention may be designed for injecting and/or collecting fluid into or from an organ or the circulatory system, for example to enable the injection of medicinal substances. According to one particular variant of this application, said device 1 may be adapted to forming an artificial vein or artery which the practitioner can pierce through the skin as with a natural vein in order to inject a therapeutic substance or collect blood.

The device 1 of the invention can also be adapted to feeding implanted reservoirs, associated for example with insulin or antalgic pumps.

Said device 1 can finally be adapted to injecting and removing fluid into and from the inflatable compartment of a surgical implant such as an artificial sphincter, a balloon or again a gastric ring designed to constrict the stomach in order to combat obesity.

Here below, the device 1 shall be considered more particularly to be a hypodermic device, i.e. a device designed to be positioned just beneath the patients' skin, although said device 1 can if necessary be implanted at other places in the patients' body and at a deeper level without departing from the scope of the invention.

According to the invention, the device 1 has a chamber 2 designed to receive the fluid substance that is injected or collected.

Said chamber 2 is demarcated by a wall 3 which has at least one penetrable portion 4 at which said wall 3 can be pierced in the direction of its thickness e by a needle 5 designed to inject or collect fluid substance into or from the chamber 2.

The penetrable portion 4 thus forms a removal area designed to ensure the imperviousness of the device 1, during piercing by the needle 5 and the transfer of fluid as well as after the withdrawal of said needle 5.

Preferably, the penetrable portion 4 is formed by a septum made out of a self-sealing material capable of being perforated by the needle. The term "self-sealing material" refers to a material having intrinsic properties of elasticity which make it capable especially of automatically closing the hole caused in it by the piercing, after the needle is extracted.

In a particularly preferable way, said penetrable portion 4 is formed by a septum made of biocompatible elastomer such as silicone and, for the convenience of this description, could be identified here below with said septum.

According to the invention, the device 1 also has means 10 for transversally compressing the penetrable portion 4, said transversally compressing means 10 being arranged so as to stress said penetrable portion 4 compressively, along at least one first substantially transversal direction D1 within the thickness e of the wall 3.

Advantageously, the compressing means 10 are used to exert and maintain a compressive pre-stress F1 within the septum, the effect of which is to improve the imperviousness of the septum in facilitating and accelerating especially its self-healing process after the withdrawal of the needle.

In particular, the transversal compression is exerted along a first direction D1 that is substantially perpendicular to the path taken by the needle 5 through the wall 3 to penetrate the chamber 2.

Thus, if the direction of penetration of the needle is taken to be substantially normal to the internal surface 4I of the penetrable portion 4, which is oriented towards the interior of the chamber 2, and/or normal to the external surface 4E of said penetrable portion, the first direction D1 of application of the compressive force F1 could be substantially parallel to either of said surfaces 4I, 4E.

In addition, the compressive pre-stress F1 is advantageously exerted permanently, whether or not the chamber 2 is filled with fluid substance: i.e. in a manner that is substantially lasting and independent of the pressure prevailing in said chamber.

Preferably, as illustrated in FIGS. 1, 2, 6 and 7, the penetrable portion 4 has a generally convex shape relatively to the exterior so as to permit access to the chamber 2 from the exterior of the device 1 along a total angular sector that is greater than or equal to 90°, preferably greater than or equal to 180°, and in a particularly preferable way, substantially equal to 360°.

In other words, the accumulated angular coverage of the removal area about the device advantageously offers lateral access to said device along a wide variety of directions of approach of the needle 5 and preferably throughout the rim of the device 1.

Naturally, the number of penetrable points 4, their spatial arrangement and the geometry of each are in no way restricted.

In particular, the convexity of the chamber 2 and of the penetrable portion 4 may be obtained by means of a continuous incurvated septum or again a plurality of distinct septums creating a plurality of facets of access to the chamber.

According to one preferred embodiment, the penetrable portion 4 forms a substantially cylindrical sleeve surrounding the chamber 2. The penetrable portion 4 thus takes the form of a hollow cylinder, preferably made in one piece. For the convenience of the description, the penetrating portion 4 could be identified here below with a sleeve.

The term "cylinder" in this case designates any solid piece obtained by the extrusion of a base surface along a generatrix.

Naturally, the geometry of the base surface is in no way restricted, and can be for example polygonal, elliptical or circular, having a constant or variable section along the generatrix.

In particular, the device 1 and especially the chamber 2 may, on the whole, have a generally straight, ovoid, ellipsoid, pyriform or polyhedral cylindrical shape.

Advantageously, the use of a substantially cylindrical septum gives the device 1 a relatively simple, compact, light and atraumatic structure that remains accessible even in the event of an overturning of the implantable site.

In a particularly preferred manner, as illustrated in the figures, the generatrix of the sleeve corresponds to a rectilinear generator axis (ZZ'), the base section being formed by a ring in such a way that the chamber 2 is demarcated by a wall 3 substantially forming a straight and hollow cylinder.

Preferably, as illustrated in FIGS. 1, 2, 6 and 7, the generator axis (ZZ') of the sleeve forming the penetrable portion 4 is substantially parallel to the first direction D1 along which said penetrable portion 4 is stressed in compression by the transversally compressing means 10.

Preferably, the sleeve is crushed in compression substantially along its generator axis (ZZ') by the transversally compressing means 10. These means tend to force the mutual approaching of its ends 4A, 4B which preferably correspond to the edges of the penetrable portion 4 placed in a position substantially normal to the generator axis (ZZ').

To this end, the transversally compressing means 10 may especially include means for holding the ends of the sleeve, such as a first flange 11 and a second flange 12 that take support respectively on the first and second ends of the sleeve 4A, 4B, said flanges being stressed in an up-closing sense, along the generator axis (ZZ') by an appropriate mechanical element such as a tie-rod.

Preferably, the first and second flanges 11, 12 are made out of a rigid, solid and perforation-resistant material.

According to a major characteristic of the invention, the device 1 is also provided with retaining means 20 designed to counter the buckling of the penetrable portion 4 towards the exterior of the device 1 under the effect of the compression exerted by the transversally compressing means 10.

Advantageously, the retaining means 20 are used to limit or even prevent the deformation of the penetrable portion 4 by the outward curvature of the chamber 2 when said penetrable portion is subjected to the transversally compressive force F1 and especially to compression at the ends exerted by the first and second flanges 11, 12.

Advantageously, the retaining means 20 may considerably limit the shear force that affects the septum during the extraction of the needle 5 as well as the fatigue stress related to the alternate stresses to which the septum is subjected by repeated motions of penetration and extraction of said needle 5. The lifespan of the site is thereby increased.

Moreover, the combination of the transversally compressing means 10 and the retaining means 20 of the invention improves the imperviousness of the penetrable portion 4 on an extensive area while nevertheless ensuring the mechanical worthiness of the device 1. This combination especially ensures that the wall 3 and of the chamber 2 undergo little deformation, both at rest and during the insertion or withdrawal of the needle 5.

In particular, it becomes possible, while preserving high imperviousness, to give the penetrable portion 4 a wide expanse despite a relatively small thickness e.

Thus, the expanse of the penetrable portion 4 measured along the first transversal direction D1 is preferably greater than the thickness e of said penetrable portion 4. In particular, the "height" h of the sleeve measured along the generator axis (ZZ'), may be at least twice, three times or even five times greater than the thickness e.

The accessibility to the chamber can therefore be optimized without in any way thereby increasing the overall space requirements and especially the diameter of the device 1.

According to a preferred alternative embodiment, with the penetrable portion 4 extending between a first end 4A and a second end 4B, the retaining means 20 comprise at least one external supporting element 21 placed opposite the chamber 2 relatively to the penetrable portion 4, between the first and second ends 4A, 4B to form a stop against said penetrable portion 4.

Advantageously, an external supporting element 21 of this kind is capable of exerting a substantially radial and centripetal retaining force F2, preferably against the external face 4E of the penetrable portion 4 and at a distance from its ends, that prevents or at any rate restricts the centrifugal radial deformation in its "central" region which is most affected by the buckling.

Thus, the external supporting element 21 forms a mechanical supporting element which supports the penetrable portion 4 from the exterior in order to form an obstacle to the free centrifugal movement into which the penetrable portion 4 can be taken by the buckling phenomenon.

Preferably, the supporting element 21 comprises at least one hooping element such as a hooping ring that gets superimposed on the wall 3 in substantially matching the external contour of the penetrable portion 4.

Naturally, said hooping element or elements is or are substantially rigid and at least more rigid, therefore more resistant to deformation under mechanical stress than the constituent material of the septum, and are preferably distinct and detachable from said septum.

The hooping element or elements are preferably positioned substantially perpendicularly to the generator axis (ZZ'). of the sleeve and if necessary are staged along said axis.

According to an embodiment corresponding to FIGS. 1 and 2, the supporting element 21 has a plurality of separate hooping rings that get superimposed on the wall 3 in substantially matching the external contour of the penetrable portion 4.

According to this preferred embodiment, the hooping rings are housed in annular grooves hollowed out on the external surface 4E of the sleeve at a distance from one another and substantially gripp the entire perimeter of the wall 3.

Thus, the buckling of the sleeve forming the penetrable portion 4 is on the whole limited by dividing the total height of the sleeve, measured along the generator axis (ZZ') into several fictitious sections of lesser height, at which the buckling is locally less pronounced.

In other words, the hooping elements enable the definition of nodes at the level of the penetrable portion 4 without however being likely to impair the physical integrity of the septum and especially its continuity, the free spaces of the septum made between said hooping elements for their part forming the undersides of said penetrable portion liable to get deformed slightly towards the exterior under the affect of the transversal compression.

Advantageously, such an arrangement enables a septum to be implemented in only one piece despite its great height, thus simplifying manufacture and limiting the risks of leakage which would be inherent to increasing the numbers of assembling joints within the implantable site.

Naturally, those skilled in the art will be capable of assessing the number and dimensions of the hooping elements on the basis of the geometry and height of the penetrable portion 4.

According to another embodiment corresponding to FIGS. 6 and 7, the hooping element is formed by a perforated tube 22 made out of a perforation-resistant material and comprising one or more apertures 23 laid out so as to permit the passage of the needle 5.

Advantageously, the internal surface 22I of the perforated tube 22 forms the supporting element 21 capable of countering the outward deformation of the penetrable wall 4 while the access to the chamber through said tube 22 which surrounds it is preserved by the implementation of the apertures 23 which the needle can travel through in order to go through and cross said tube and then go through the penetrable portion 4 until it comes out into the chamber 2.

Preferably, as illustrated in FIGS. 1, 2, 6 and 7, the sleeve forming the penetrable portion 4 and the perforated tube 22 are substantially coaxial and preferably contiguous, the generator axis (ZZ') of the sleeve being substantially coincidental with the generatrix of said perforated tube 22.

In other words, the supporting element 21 can advantageously take the form of an open-worked sheath placed around the septum and preferably having an internal face 22I with a shape that is substantially conjugated to the external face 4E of this septum, the geometry of such a supporting element 21 being of course not limited to one particular alternative embodiment.

Preferably, the perforated tube 22 nevertheless has a straight cylindrical geometry, the apertures 23 being pierced on its curved lateral wall.

Naturally, the perforated tube 22 will be made preferably as a single piece out of a material more rigid than that of the septum, preferably biocompatible and in a particularly preferable way, it may be made of titanium, polycarbonate (PC), poly-ether-ether-ketone (PEEK), polysulfone (PSU) or any other appropriate material.

In addition, said perforated tube 22 will preferably have a substantially constant thickness as well as substantially even and smooth external and internal surfaces, 22I, 22E to ensure high comfort of use for the patient.

Advantageously, the perforated tube 22 could constitute a single hooping element covering substantially the entire external surface 4E and more particularly, the entire external lateral surface of the septum.

Advantageously, the solid zones 24 of the perforated tube 22 situated between neighboring apertures 23 firstly provide for the cohesion of said perforated tube 22 and secondly each offer a point of support against which the external surface 4E of the sleeve rests.

Increasing the numbers of supporting points between the ends 4A, 4B of the sleeve in this way advantageously reduces the range of each of the apparent zones of the septum between two consecutive supporting points, i.e. the transversal dimension of each of the areas accessible to the needle (because they are not covered by a solid zone 24) in such a way that the sensitivity to the overall buckling of said septum is considerably diminished.

Advantageously, the perforated tube 22 could form a sort of rigid exoskeleton which gives the device 1 its functional shape and substantially maintains said functional shape and more particularly the useful volume of the chamber 2 over time.

Naturally, the geometry and distribution of the apertures 23 are not limited to one particular embodiment.

Preferably, the apertures 23 are nevertheless pierced along a piercing direction that is substantially normal to the faces of the perforated tube 22 i.e. the tube is hollowed out in a direction that is substantially radial to the generator axis (ZZ').

Said apertures 23 can especially be formed by circular perforations as illustrated in FIG. 3 or again by square-shaped, rectangular or polygonal apertures as illustrated in FIG. 4.

In a particularly preferred way, as illustrated in FIGS. 5A to 5F, 8 and 7, the apertures 23 are formed by circular-sectioned perforations positioned substantially around the generator axis (ZZ') of the perforated tube 22.

In a particularly preferred way, said perforated tube 22 has a plurality of apertures 23 distributed along at least one row, i.e. substantially along a ring of constant ordinate value relatively to the generator axis (ZZ') on most of its rim or even on its entire rim.

According to an embodiment, the apertures 23 are all substantially identical and distributed within one row, equidistantly and preferably edge-to-edge at an angular pitch that is substantially constant as illustrated especially in FIGS. 5C and 5D.

By way of an example, the perforated tube shown in FIGS. 5A to 5F comprises 10 rows of twenty-five apertures each, the angular pitch being 14.40°.

Furthermore, the perforated tube 22 can be provided with several successive rows of apertures 23 staged along the generator axis (ZZ'), said rows being, in a particularly preferred manner, offset relatively to one another so as to be arranged quincunxially.

Preferably, each row has a constant angular pitch identical to that of the neighboring rows and is offset angularly by the equivalent of an angular half pitch relatively to its immediately neighboring rows.

It is thus advantageously possible to obtain a matrix arrangement of the apertures 23 which optimizes the proportion of the external surface 22E of the tube which remains permanently piercable by the needle 5 in minimizing the residual expanse of the perforation-resistant solid zones 24 which connect the neighboring apertures 23 to one another and provide for the cohesion of the perforated tube 22.

According to a particular preferred alternative embodiment corresponding to FIGS. 5A to 5F, 6 and 7, the apertures 23 comprise a chamfered portion 23A opening out toward the exterior and also adjoin each other so that the external surface 22E of the perforated tube has a honeycomb appearance.

In other words, the neighboring apertures 23 have interfering chamfered portions 23A in such a way that their resultant junction, at the external surface 22E of the perforated tube, takes the form of a ridge 25 which forms the tip of the corresponding solid zone 24. As it happens, each aperture 23 is thus demarcated at the external surface 22E of the tube by six ridges 25 distributed in a hexagon.

Naturally, the flared shape of the chamfered portions 23A is in no way restrictive, and may for example correspond to a truncated cone whose slopes are substantially rectilinear or again a horn whose slopes are substantially outwardly curved from the ridge 25 onwards.

Furthermore, the apertures 23 preferably have a straight portion 23B, advantageously cylindrical, situated in the extension of the chamfered portion towards the chamber 2 in order to ensure that the needle 5 is guided along a substantially centripetal radial direction of penetration.

Such an arrangement prevents a "tangential" perforation of the device 1 by the needle 5 in which this needle would take a direction of incidence that is flat enough to remain blocked in the thickness of the sleeve forming the penetrable portion 4 without opening out into the chamber 2.

More particularly, the shape of the apertures 23 of the invention make it possible to obtain an alveolate structure in which each aperture 23 has a "funnel" function enabling it to "take in" the incident needle 5 in the wide section of the chamfered portion 23A and then make it converge by gradually turning it down towards the gripped straight section which guides it in turn through the thickness of the perforated tube and then through the septum up to the center of the chamber 2.

By way of an indication, the depth of the chamfered portion could be about one third of the thickness of the wall of the perforated tube 22 while the straight portion 23B will represent about the remaining two-thirds of this same thickness.

Naturally, the dimensions of the straight portion 23B and especially its diameter and its guidance range will depend on each other and be determined on the range of diameters of the needles 5 which are to be used with the device 1.

As shown in FIGS. 1, 2, 6 and 7, the first flange 11 is preferably designed to be fixed to the perforated tube 22 and to form a stop countering the shift of the sleeve forming the penetrable portion 4 along the generator axis (ZZ').

According to a particularly preferred embodiment, said first flange 11 forms one piece with the perforated tube 22 and may be advantageously situated at its end so as to form the bottom of said perforated tube 22. Said tube then takes the appearance of a blind-end shell.

According to an alternative preferred embodiment corresponding to FIGS. 6 and 7, the second flange 12 can be assembled by being screwed into the perforated tube 22 and have a portion 12A laid out so as to protrude into said tube and be supported against the sleeve forming the penetrable portion 4, substantially opposite the first flange 11.

The septum is thus sandwiched along the generator axis (ZZ') between the first and second flanges.

In order to prevent said second flange 12 from forming a radial projection beyond the extension of the external lateral surface 22E of the perforated tube 22, said tube is preferably provided with an internal thread 26 with which there cooperates an external thread cut into the periphery of the projecting portion 12A of the flange. This ensures the compactness of the site as well as the evenness of its apparent surface and its atraumatic character.

Advantageously, the layout according to the invention gives the site 1 a particularly simple and compact structure whose assembly is both easy and unaffected by the manufacturing tolerances of the perforated tube or the septum.

Indeed, said assembly is made by threading or nesting the septum quite simply within the perforated tube 22 and then attaching the second flange 12 in the manner of a ring screwed onto said tube, the screwing in of said second flange 12 advantageously adjusting the degree of compression of said septum in compensating for possible differences in dimensions, especially the height, related to random factors in the manufacture of said septum.

It is noteworthy that, according to one characteristic which may constitute an invention in itself, the transversally compressing means 10 are advantageously adjustable so as to enable, at least during the assembling of the device 1, the adjustment, in this case continuously, of the transversally compressive pre-stressing F1 which they exert on the penetrable portion 4.

In particular, the transversally compressive means 10 may be sized (just like the septum) so as to prompt a longitudinal contraction of the septum of about 5% to 10% of its height at rest.

Furthermore, as illustrated in FIGS. 2 and 6, the second flange 12 may advantageously serve to support a nozzle 30 enabling the device to be attached to a catheter (not shown) and to the chamber that is put into communication with this catheter.

Preferably, said nozzle 30 is centered relatively to the second flange 12 and aligned with the perforated tube 22 and the sleeve along the generator axis (ZZ').

According to an embodiment, the device of the invention has an anti-perforation shield 31 positioned in the chamber 2 so as to prevent a needle 5 penetrating said chamber 2 by an entry point situated in the penetrable portion 4 from crossing the device 1 from one side to the other and emerging at an exit point in again going through the penetrable point 4 substantially opposite the entry point, especially when the penetrable portion 4 has a large expanse or an outwardly curved shape.

Preferably, said anti-perforation shield has a plurality of plates positioned substantially in parallel to the generator axis (ZZ') contiguous to one another at one of their ends and oriented substantially radially relatively to the generator axis so as to form a star, for example, a six-pointed star.

Preferably, said plates will extend substantially throughout the height h of the septum from this first flange 11 up to the second flange 12.

In this respect, it is noteworthy that the second flange 12 will preferably have a central clearance 32 creating a passage for the shield 31 so that the projecting portion 12A of the flange can take support in a substantially ringed arrangement on the sleeve and thus enable a clamping under stress of said sleeve without the second flange 12 prematurely abutting the anti-perforation shield 31 and being blocked by it during the screwing-in process.

Preferably, the anti-perforation shield 31 is made out of a rigid material such as titanium so as to strengthen the structure of the device 1 and especially provide an additional support to the septum.

It is advantageously possible to prevent the centripetal radial deformation of the sleeve i.e. to substantially maintain the functional volume of the chamber 2 in preventing the chamber from being crushed when the needle 5 is introduced.

Furthermore, an arrangement of this kind contributes to preventing the buckling of the penetrable portion 4 into the chamber 2 under the effect of the transversal compression F1.

Furthermore, as illustrated in FIG. 1, the septum may be provided with longitudinal grooves 33 designed to receive the free ends of the plates of the shield.

Besides, the site 1 preferably has an external envelope 34 made for example out of silicone in order to perfect the cladding and the atraumatic finish of said implantable site 1. The wall of the site 1 then has a multilayered structure, the perforated tube 22 being positioned between the external envelop 34 and the septum 4.

According to one alternative embodiment which may constitute an invention on its own, the implantable site 1 may be provided with means for compressing the septum in two directions, these means being capable of exerting compression on and simultaneously keeping the penetrable portion 4 under compression substantially in the sense of its thickness e, i.e. substantially along the predictable direction of penetration of the needle 5, in this case a substantially radial direction but also along at least one of the directions transversal to this thickness, i.e. along a direction substantially perpendicular to the direction of penetration of the needle 5, in this case in a substantially longitudinal direction.

More particularly, the retaining means 20 may be laid out to compressively pre-stress the penetrable portion 4 of the wall 3 in the direction of its thickness e.

To this end, the septum may advantageously be caged in the perforated tube 22, i.e. the external diameter at rest of the sleeve forming the penetrable portion 4 is, prior to assembly, strictly greater than the internal diameter of said perforated tube 22, for example 5% to 15% and preferably 6% to 10%.

An assembly of the two elements can thus be obtained by force-fitting or press-filing, with the appearance of a residual stress of centripetal radial elastic deformation which lastingly compresses the sleeve inside the perforated tube.

Combining this kind of force-fitting with the longitudinal compressing that takes place when the second flange 12 is screwed in advantageously procures a state of bidirectional pre-stressing of the septum within the perforated tube 22.

In other words, the retaining means 20 and especially the supporting element 21 are preferably not passive and their function goes beyond a simple retaining function, i.e. they do not just "passively" exert a simple retaining stress F2 only when the penetrable portion 4 is subjected to buckling. They well and truly exert an active compressive stress that is sufficient to elastically deform the septum. They do this as soon as they are assembled and independently of whether or not there exists a transversally compressive stress F1.

Advantageously, the retaining means 20 are themselves capable of exerting a non-zero compressive stress F2, in this case a centripetal and radial stress, on the external surface 4E of the penetrable portion 4 and preferably substantially on all of said external surface so as to obtain a constriction of the sleeve.

In this respect, the presence of an anti-perforation shield 31 advantageously makes it possible to limit the contraction of the internal diameter of the sleeve and therefore to both maintain the functional volume of the chamber 2 and improve the placing of said sleeve under compression in the direction of its width.

Besides, it is noteworthy that this improvement of the imperviousness by bi-directional compression of a septum, simultaneously along the direction of penetration of the needle and along at least one direction substantially perpendicular to said direction of penetration, could advantageously be implemented in other applications requiring a self-sealing system of removal as in the case for example of the plugging of flasks containing a substance, for example a therapeutic substance, that has to be preserved from its environment.

Purely by way of a non-exhaustive indication, the device 1 of the invention may have substantially the following dimensions and proportions, in the particular case of a device suited to a hollow needle with a diameter of 0.9 mm:

- sleeve at rest (before compression): external diameter equal to 15 mm, wall thickness equal to 3.5 mm, length (measured along the generator axis) equal to 19 mm;
- pre-stressed assembled sleeve: external diameter equal to 14 mm, thickness equal to 3.35 mm, length equal to 17.5 mm;
- perforated tube: overall length equal to 20.5 mm, internal diameter equal to 14 mm, wall thickness ranging from 0.8 mm to 2 mm and preferably in the region of 1.5 mm;
- diameter of the perforation of the apertures in the straight portion equal to 1.4 mm;
- chamfered portion of the apertures: 0.4 mm×45° to 0.5 mm×45°;
- linear pitch of staging of the rows of apertures: 3.20 mm for 10 rows.

Naturally, the device 1 of the invention will be adapted to one or more of the standard formats of hollow needles used for the corresponding application, and the diameter of the apertures 23 will naturally be determined accordingly.

In this respect, the device 1 could be provided with a marking, possibly embossed and/or radio-opaque enabling the practitioner immediately, before and/or after implantation, to recognize the hollow needle formats compatible with the said device 1.

Naturally, the invention also pertains as such to a medical kit comprising firstly at least one device according to the invention and secondly a set of hollow needles 5 of a diameter adapted to said device.

A method for manufacturing an implantable medical device 1 according to the invention shall now be described in brief.

The method of manufacture according to the invention comprises at least one step (a) of transversal compressive pre-stressing during which the compressing of the penetrable device 4 is prompted along at least one first direction D1 that is substantially transversal to the direction of its thickness as well as a retaining step (b) during which the free buckling of the penetrable portion 4 towards the exterior of the device, under the effect of transversal compression, is countered.

Preferably, the retaining step (b) comprises a sub-step (b1) for setting up support during which a supporting element 21 is placed against the penetrable portion 4 so as to hinder the deformation and movement of this portion under the effect of the transversally compressive pre-stress F1.

Preferably, the sub-step (b1) for setting up support is made by slipping a hooping element around the sleeve so as to grip this sleeve.

Preferably, during the sub-step (b1) for setting up support, the entire external surface 4E of the penetrable portion 4 is substantially covered, for example by means of a sheath-forming perforated tube.

Preferably, the compressive pre-stressing step (a) is obtained in two stages, first of all by placing the sleeve so that it abuts a first flange 11 forming the bottom of the perforated tube 22 and then by attaching a second flange 12 to the other end of said tube 22, this second flange 12 penetrating said tube until it compresses the opposite end of the sleeve which had hitherto remained free.

Preferably, the compressive pre-stressing step (a) may be preceded by a shield-insertion step during which an anti-perforation shield 31 is slipped into the chamber 2, i.e. into the hollow of the sleeve, preferably after said sleeve has been slipped into the perforated tube 22.

It is then that the assembly formed by the sleeve and the anti-perforation shield is trapped and mounted in a gripped manner in the cage formed by the perforated tube 22 during the step (a) of compressive pre-stressing, in attaching and screwing in, at the end, the second flange 12 which has crushed the sleeve by elastic deformation along the generator axis (ZZ'). Once the desired level of pre-stressing has been achieved, the immobilizing of the flange substantially ensures that it is maintained.

It is noteworthy that, according to one characteristic which may constitute an invention on its own, the assembling method of the invention may include a step for successive nesting operations during which a cylindrical septum 4 is attached inside a perforated tube 22 so as to be substantially coaxial with said tube followed possibly by the insertion of an anti-perforation screen 31, also coaxial with the above-mentioned elements, followed by a step for closing the assembly by means of a lid formed by the second flange 12.

Preferably, the method of manufacture according to the invention includes a step (c) for compressing the septum in the direction of its thickness. This is preferably obtained by attaching, within the perforated tube 22, a cylindrical septum with a diameter at rest that is greater than the interior diameter of said tube within said perforated tube 22, for example by force-fitting, or again by press-fitting, so as to force the radial and centripetal elastic contraction of the sleeve within and in contact with the perforated tube of smaller diameter.

Naturally, the method of assembly of the invention will preferably include a step (d) for manufacturing the septum during which a cylindrical sleeve, with a diameter at rest that is substantially greater than that of the perforated sleeve, will be made, for example by molding.

The method of manufacture will also preferably comprise a step for making the perforated tube 22, for example by machine-turning, during which first of all a blind-end cylinder and then radial piercings will be made so as to form an alveolate structure, permeable to perforation, on the curved wall of said cylinder.

To this end, it is also possible to use a staged drill in order to simultaneously, for each aperture 23, makes the straight portion 23B and the milling corresponding to the chamfered portion 23B.

Advantageously the manufacturing method according to the invention enables the making of a site having substantially a geometry generated by revolution about its generator axis (ZZ'), which greatly facilitates its assembling and also improves its accessibility.

Moreover, despite its solidity, the site 1 remains compact, largely and permanently accessible, without requiring any particular intervention by the practitioner.

In addition, the design of the device 1 according to the invention in which the septum is compressed both radially and longitudinally makes it possible during assembly, to compensate for variations in manufacture in terms of quality of silicone whose hardness generally varies by about +/−5 Shore A in a same batch or again in terms of dimensions of molded parts such as the septum. It is thus possible to routinely assemble any septum with any perforated tube without its being necessary to preliminarily sort out these parts to ensure their compatibility.

Finally, the implantable site according to the invention has a substantial functional volume of chamber while at the same time preserving overall compactness. In particular, the thickness of the septum may advantageously be reduced, impairing neither the behavior under crushing of said chamber during the piercing operation or during movements made by the patient nor the imperviousness of the site.

The invention claimed is:

1. Implantable medical device for injecting and/or collecting fluid substance into or from a human or animal organism, the device comprising
   a chamber for receiving said fluid substance, said chamber being demarcated by a wall which has at least one penetrable portion at which said wall can be pierced through in the direction of its thickness by a needle designed to inject and/or remove the fluid substance into or from the chamber, said device comprising a compressor configured to transversally compress the penetrable portion the compressor being arranged so as to stress said penetrable portion compressively along a first direction that is substantially transverse to the direction of thickness of the wall,
   wherein:
   the device is provided with a retainer designed to counter the buckling of the penetrable portion towards the exterior of the device under the effect of the compression exerted by the compressor;
   in that the penetrable portion extends, in the first transversal direction, between a first end and a second end, and in that the retainer comprises at least one external supporting element placed opposite the chamber relatively to the penetrable portion between the first and second ends to form a stop against said penetrable portion;
   and in that the retainer is capable itself of exerting a non-zero, radial and centripetal compressive stress on the external surface of the penetrable portion.

2. Device according to claim 1, wherein the penetrable portion of the wall is formed by a septum made of elastomer.

3. Device according to claim 1 wherein the expanse of the penetrable portion measured along the first direction is greater than its thickness.

4. Device according to claim 1, wherein the penetrable portion has a generally convex shape so as to permit access to the chamber from the exterior of the device along a total angular sector that is greater than or equal to 90°.

5. Device according to claim 4, wherein the penetrable portion forms a substantially cylindrical sleeve surrounding the chamber.

6. Device according to claim 5, wherein the generator axis of the sleeve is substantially parallel to the first direction along which said penetrable portion is stressed in compression.

7. Device according to claim 1, wherein the supporting element comprises at least one hooping element that gets superimposed on the wall in substantially matching the external contour of the penetrable portion.

8. Device according claim 7, wherein the hooping element is formed by a perforated tube made out of a perforation-resistant material and comprising one or more apertures laid out so as to permit the passage of the needle.

9. Device according to claim 8, wherein the apertures are formed by circular-sectioned perforations positioned substantially around the generator axis of the perforated tube.

10. Device according to claim 9, wherein the apertures comprise a chamfered portion opening out toward the exterior and adjoining each other so that the external surface of the perforated tube has a honeycomb appearance.

11. Device according to claim 6, wherein the sleeve forming the penetrable portion on the one hand and the perforated tube on the other hand are substantially coaxial.

12. Device according to claims 8, wherein the compressor comprises a first flange designed to be fixed to the perforated tube and to form a stop countering the shift of the sleeve.

13. Device according to claim 12 wherein the first flange forms one piece with the perforated tube.

14. Device according to claim 12, wherein the compressor comprise a second flange assembled by being screwed into the perforated tube and having a portion laid out so as to protrude into said tube and be supported against the sleeve forming the penetrable portion, substantially opposite the first flange.

15. Device according to claim 1, wherein the retainer is laid out to compressively pre-stress the penetrable portion of the wall in the direction of its thickness.

16. Device according to claim 1, wherein the external diameter at rest of the sleeve forming the penetrable portion is, prior to assembly, strictly greater than the internal diameter of said perforated tube.

* * * * *